US006410743B2

(12) United States Patent
Li et al.

(10) Patent No.: US 6,410,743 B2
(45) Date of Patent: Jun. 25, 2002

(54) TETRAHYDRONAPHTALENE DERIVATIVES AND THEIR USE

(75) Inventors: Ming Li, Mobile, AL (US); John Bondo Hansen, Jyderup; Tina Moller Tagmose, Ballerup, both of (DK)

(73) Assignees: Novo Nordisk A/S, Bagsvaerd (DK); South Alabama Medical Science Foundation, Mobile, AL (US)

( * ) Notice: Subject to any disclaimer, the term of this patent is extended or adjusted under 35 U.S.C. 154(b) by 0 days.

(21) Appl. No.: 09/818,392

(22) Filed: Mar. 27, 2001

Related U.S. Application Data

(63) Continuation of application No. PCT/DK01/00129, filed on Feb. 23, 2001.
(60) Provisional application No. 60/185,294, filed on Feb. 28, 2000.

(30) Foreign Application Priority Data

Feb. 25, 2000 (DK) .......................................... 2000 00294

(51) Int. Cl.[7] .................. C07D 233/54; A61K 31/4184
(52) U.S. Cl. ................. 548/309.7; 548/310.1; 514/394
(58) Field of Search ........................... 548/309.7, 310.1; 514/394

(56) References Cited

U.S. PATENT DOCUMENTS

| 4,808,605 A |   | 2/1989 | Branca et al. ............... 514/394 |
| 4,808,650 A |   | 2/1989 | Titus et al. .................. 524/108 |
| 5,633,377 A | * | 5/1997 | Thurkauf et al. ........... 544/370 |

FOREIGN PATENT DOCUMENTS

| WO | WO 00/02543 | 1/2000 |
| WO | WO 00/15845 | 3/2000 |

OTHER PUBLICATIONS

S. Verma et al., "Chronic T–type Ca2+ channel blockade with mibefradil in hyperinsulinemic insulin–resistant and hypertenive rats"—Cardiovascular Research, vol. 34, pp. 121–128 (1997).
Cribbs et al., Circ. Res., vol. 83, pp. 103–109 (1998).
Joseph Levy, Endocrine, vol. 10, pp. 1–6 (1999).
Bjork et al., Diabetes, vol. 45, pp. 1427–1430 (1996).
Hiriart et al., The Journal of General Physiology, vol. 91, pp. 617–639 (1988).
Vague et al., Metabolism, vol. 31, pp. 139–142 (1982).
William A. Catterall, Science, vol. 253, pp. 1499–1500 (1991).
William A. Catterall, Science, vol. 242, pp. 50–61 (1988).
Davalli et al., Journal of Endocrinology, vol. 150, pp. 195–203 (1996).
Karlsson et al., Autoimmunity, vol. 26, pp. 117–122 (1997).
Keahey et al., Diabetes, vol. 38, pp. 188–193 (1989).
Bhattacharjee et al., Endocrinology, vol. 138, pp. 3735–3740 (1997).
Kato et al., Metabolism, vol. 43, pp. 1395–1400 (1994).
Kato et al., J. Clin. Invest., vol. 97, pp. 2417–2425 (1996).
Seino et al., Biochemistry, vol. 89, pp. 584–588 (1992).
Perez–Reyes et al., Nature, vol. 391, pp. 896–900 (1998).
Zhuang et al., Diabetes, vol. 49, pp. 59–64 (2000).

* cited by examiner

*Primary Examiner*—Floyd D. Higel
*Assistant Examiner*—Kamal Saeed
(74) *Attorney, Agent, or Firm*—Reza Green, Esq.; Peter J. Waibel, Esq.

(57) ABSTRACT

Tetrahydronaphatalene derivatives, and compositions comprising the compounds. The tetrahydronaphatalene derivates are useful in inhibiting a rise in intracellular calcium mediated by an influx through T-type calcium channels, and are thus useful for treatment of, for example, type 1 and type 2 diabetes and cardiovascular diseases associated with diabetes.

18 Claims, No Drawings

TETRAHYDRONAPHTALENE DERIVATIVES AND THEIR USE

CROSS-REFERENCE TO RELATED APPLICATIONS

This application is a continuation of PCT/DK01/00129 filed Feb. 23, 2001 and claims priority under 35 U.S.C. 119 of Danish application PA 2000 00294 filed Feb. 25, 2000, and U.S. provisional application 60/185,294 filed on Feb. 28, 2000, the contents of which are fully incorporated herein by reference.

FIELD OF THE INVENTION

The present invention relates to novel tetrahydronaphtalene derivatives, to compositions comprising these compounds and their use in therapy, e.g. in the treatment and in the prevention of type 1 and type 2 diabetes as well as cardiovascular disorders associated with diabetes.

BACKGROUND OF THE INVENTION

Insulin secretion from pancreatic β-cells is the primary physiological mechanism of blood glucose regulation. A rise in blood glucose concentration stimulates release of insulin from the pancreas, which in turn promotes glucose uptake in peripheral tissues and consequently lowers blood glucose levels, reestablishing euglycemia. Non-insulin dependent diabetes mellitus (NIDDM)(type II diabetes) is associated with impairment in glucose-induced insulin secretion in pancreatic β-cells (Vague, P. and Moulin, J. P., Metabolism 31:139–144 (1982)).

Voltage-gated $Ca^{2+}$ channels mediate a rapidly activated inward movement of $Ca^{2+}$ ions that underlies the stimulation of insulin secretion in β-cells (Boyd, A. E. III, Current Concepts, The Upjohn Company, Kalamazoo, Mich. (1991). In different tissues, four types of $Ca^{2+}$ channels have been described (L(P/Q), T, N, and E channels). The purified L-type $Ca^{2+}$ channel consists of five subunits: $\alpha_1$, $\alpha_2$, β, γ, δ (Catterall, W. A., Science 253:1499–1500 (1991)). The primary structure of the $\alpha_1$ subunit is organized in four homologous domains containing six transmembrane segments (Catterall, W. A., Science 242:50–61 (1988).

Rat and human pancreatic β-cells are equipped with L-type and T-type $Ca^{2+}$ channels (Hiriart, M. and Matteson, D. R., J Gen Physiol 91:145–159 (1988); Davalli, A. M., et al., J Endocrinology 150:195–203 (1996)). L-type $Ca^{2+}$ channels, activated at high voltages and having large unitary conductance and dihydropyridine-sensitivity, are considered the major pipe-line for $Ca^{2+}$ influx into the β-cell (Keahey, H. H., et al., Diabetes 38:188–193 (1989)). In contrast, T-type calcium channels activate at low voltages and have small unitary conductance and dihydropyridine-insensitivity.

The physiological function of T-type $Ca^{2+}$ channels in β-cell insulin-secretion has been demonstrated (Bhattacharjee, A., et al., Endocrinology 138:3735–3740 (1997). These channels facilitate exocytosis by enhancing electrical activity in these cells. L-type and T-type $Ca^{2+}$ channels, under normal conditions, work in concert promoting the rise in $[Ca^{2+}]_i$, during glucose-stimulated insulin secretion. In β-cells, over-expressed T-type $Ca^{2+}$ channels may be, at least in part, responsible for the hyper-responsiveness of insulin secretion to non-glucose depolarizing stimuli in GK rat and in rat with NIDDM induced by neonatal injection of streptozotocin (Kato, S., et al., Metabolism 43:1395–1400 (1994); Kato, S., et al., J Clin Invest 97:2417–2425 (1996)). However, over-expressed T-type calcium channels over time will ultimately lead to an elevation of basal $Ca^{2+}$ through it's window current properties. Therefore, there is a dual effect of T-type $Ca^{2+}$ channels in β-cells depending upon channel number and membrane potential.

Two isoforms of L-type $Ca^{2+}$ channel α1 subunits have been identified in β-cells (Seino, S., et al., Proc Natl Acad Sci USA 89:584–588 (1992)). The rat neuronal T-type calcium channel has been cloned (Perez-Reyes, E., et al., Nature 391:896–900 (1998)). The α1G subunit of the T-type calcium channel has been cloned from the rat insulin secreting cell line INS-1 (Zhuang et al., Diabetes 49: 59–64, 2000). This α1G subunit is expressed in rat islets as well as in brain, neonatal heart and kidney. The α1 H subunit of the T-type calcium channel has been cloned from human heart (Cribbs, L. L. Circ. Res. 83: 103–109 (1998). Other subunits of T-type $Ca^{2+}$ channel have yet to be identified.

It has recently been described that the blocker of T-type and L-type calcium channels mibefradil prevents and reverses the development of hypertension, hyperinsulinemia and hypertriglyceridemia in fructose fed rats (S. Verma et al, Cardiovascular Research 34: 121–128 (1997)).

In patients suffering from type 2 diabetes and in animal models of type 2 diabetes, an elevated intracellular level of calcium in both beta-cells and non-pancreatic tissue has been observed (J. Levy, Endocrine, 10: 1–6 (1999). It is believed that compounds able to inhibit a rise in intracellular calcium are useful to treat or prevent type 2 diabetes, and microvascular or macrovascular diseases associated with diabetes.

Blockers of T-type channels of pancreatic beta cells protect these cells from the cytotoxic effects of cytokines and reduce basal insulin release to reduce the presentations of antibodies associated with Type 1 diabetes. These effects can be used in the treatment on patients suffering from Type 1 diabetes as described by Karlsson and Bjork (*Diabetes* 45:1427–30 (1996) and *Autoimmunity* 26:117–122 (1997)).

U.S. Pat. No. 4,808,650 discloses mibefradil and analogues thereof as calcium antagonists which are useful in the treatment of angina pectoris, ischaemia, arrhythmias, high blood pressure and cardiac insufficiency.

The present invention provides a class of novel tetrahydronaphtalene derivatives which is able to inhibit a rise in intracellular calcium mediated by an influx through T-type calcium channels, indicating that the compounds of the present invention are useful in the treatment and in the prevention of diabetes and microvascular or macrovascular diseases associated with diabetes.

SUMMARY OF THE INVENTION

The present invention relates to novel tetrahydronaphtalene derivatives of the general formula (I) wherein $R^1$, $R^2$ and $R^3$ are as defined in the detailed part of the present description.

The present compounds interfere with T-type calcium channel activity and can be used for treating and for preventing type 1 and type 2 diabetes and diabetic cardiovascular disorders.

Further, the present compounds are particularly well suited to blocking (inhibiting) the activity of T-type calcium channels but not blocking the activity of L-type calcium channels.

Further provided are pharmaceutical compositions comprising the compounds of the general formula I or a pharmaceutically acceptable salt thereof together with a pharmaceutically acceptable carrier or diluent.

The invention further provides methods of treating and methods of preventing type 1 and type 2 diabetes, as well as methods of treatment and methods of preventing microvascular or macrovascular diseases associated with diabetes, in a subject (human or animal), the method comprising administering to the subject an amount of a compound effective to modify levels of T-type calcium channels in the pancreatic beta cells and non-pancreatic tissue of the subject.

DETAILED DESCRIPTION OF THE INVENTION

Accordingly, the present invention relates to novel tetrahydronaphtalene derivatives of the general formula (I)

(I)

wherein $R^1$ is H, $C_{1-6}$-alkyl or phenyl which is optionally substituted with halogen, methoxy or $C_{1-6}$-alkyl; and $R^2$—C—$R^3$ together forms a $C_{3-6}$-cycloalkyl group; or a pharmaceutically acceptable salt thereof with a pharmaceutically acceptable acid or base.

The present invention also encompass any pharmaceutically acceptable salts, esters, or salts of such esters, or any other of the present compounds which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the present invention, pharmaceutically acceptable salts of such prodrugs, and other bioequivalents.

In regard to prodrugs, the compounds of the present invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions.

In regard to pharmaceutically acceptable salts, the term pharmaceutically acceptable salts refers to physiologically and pharmaceutically acceptable salts of the compounds of the present invention: i.e., salts that retain the desired biological activity of the parent compound and do not impart undesired toxicological effects thereto. These salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The terms "$C_{1-6}$-alkyl" as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, n-hexyl, 1,2-dimethylpropyl, 2,2-dimethylpropyl, 1,2,2-trimethylpropyl and the like.

The term "halogen" as used herein means fluorine, chlorine, bromine or iodine.

The term "$C_{3-6}$-cycloalkyl" as used herein refers to a radical of a saturated cyclic hydrocarbon with the indicated number of carbons such as cyclopropyl, cyclobutyl, cyclopentyl, or cyclohexyl.

In one embodiment of the invention $R^1$ is H.

In another embodiment of the invention $R^1$ is methyl.

In another embodiment of the invention $R^2$—C—$R^3$ together forms a cyclopropyl group.

In another embodiment of the invention $R^2$—C—$R^3$ together forms a cyclobutyl group.

Specific compounds of the invention are:

(1S,2S)-2-(2-{N-[(3-benzoimidazol-2-yl)propyl]-N-methylamino}ethyl)-6-fluoro-1 2,3,4-tetrahydro-1-isopropyl-2-naphtyl cyclopropanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclobutanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclopentanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclohexanecarboxylate;

(1S,2S)-2-(2-{N-[(3-benzoimidazol-2-yl)propyl]-N-methylamino}ethyl)-6-fluoro-1 2,3,4-tetrahydro-1-isopropyl-2-naphtyl methylcyclopropanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl ethylcyclopropanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclobutanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl ethylcyclobutanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclopentanecarboxylate;

(1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclohexanecarboxylate; or a pharmaceutically acceptable salt thereof.

The present invention is based in part on the discovery that regulation of T-type calcium channels directly modifies basal calcium levels in cells, which in turn regulates L type calcium channel activity, which in turn regulates insulin secretion and cell death, which in turn treats e.g. type 2 diabetes. The present invention is further based on the discovery that regulation of T-type calcium channels directly affects basal and glucose-induced insulin secretion. The invention thus provides a method of modifying insulin secretion by pancreatic beta cells, the method comprising modifying levels of T-type calcium channels in the pancreatic beta cells.

Accordingly, in another aspect, the invention relates to pharmaceutical compositions comprising the compounds of the general formula I or a pharmaceutically acceptable salt thereof together with a pharmaceutically acceptable carrier or diluent.

In another aspect, the invention relates to pharmaceutical compositions for use in the treatment and/or prevention of type 1 and type 2 diabetes as well as diabetic cardiovascular disorders comprising the compounds of the general formula I or a pharmaceutically acceptable salt thereof together with a pharmaceutically acceptable carrier or diluent.

In another aspect, the invention relates to the use of a compound of the general formula I or a pharmaceutically acceptable salt thereof for the preparation of a pharmaceutical composition for the treatment and/or prevention of diseases related to the inhibition of a rise in intracellular calcium mediated by an influx through T-type calcium channels.

In another aspect, the invention relates to the use of a compound of the general formula I or a pharmaceutically acceptable salt thereof for the preparation of a pharmaceutical composition for the treatment and/or prevention of type 1 and type 2 diabetes as well as microvascular or macrovascular diseases associated with diabetes, such as retinopathy, nephropathy, neuropathy, gangrene, myocardial infarction, cerebral stroke and atherosclerosis.

In another aspect, the invention provides a method of treating and/or preventing type 1 and type 2 diabetes as well as microvascular or macrovascular diseases associated with diabetes, such as retinopathy, nephropathy, neuropathy, gangrene, myocardial infarction, cerebral stroke and atherosclerosis in a subject (human or animal), the method comprising administering to the subject an amount of a compound effective to modify levels of T-type calcium channels in the pancreatic beta cells of the subject.

For therapeutics, methods of modifying insulin secretion by pancreatic beta cells, methods of treating diabetes, methods of modifying basal calcium levels in cells, methods of modifying the action potential of L-type calcium channels in cells, methods of modifying pancreatic beta cell death, methods of modifying pancreatic beta cell proliferation, and methods of modifying calcium influx through L-type calcium channels in cells, each of the methods comprising modifying levels of functional T-type calcium channels in the cells, are provided.

In yet another aspect, the present invention relates to methods of preparing the above mentioned compounds. The methods comprises:

Reacting a compound of formula (II):

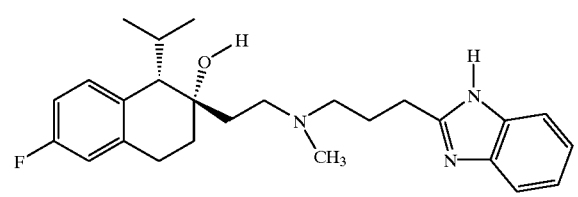

(II)

with an activated carboxylic acid of formula (III):

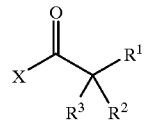

(III)

wherein $R^1$, $R^2$ and $R^3$ are defined above and X is a leaving group, such as halogen, preferentially chlorine; azide, alkoxy, phenoxy or carbonyloxy. If X is —OH, elevated temperatures and/or a catalyst such as hydrochloric acid will frequently be needed.

The compound of formula (II) may be prepared as described in Y. Crameri et al, Tetrahedron: Assymetry, 8: 3617–3623 (1997) and in U.S. Pat. No. 4,808,605 or by acid or base catalysed hydrolysis of mibefradil, using standard syntetic procedures as described in e.g. J. March: Advanced Organic Chemistry, 4.ed. 1992, McGraw Hill.

PHARMACOLOGICAL METHODS

Effect of compounds on T-type $Ca^{2+}$ channel $\alpha_1$G-INS-1 subunit expressed on Xenopus Oocytes or mammalian cells. Part 1. Xenopus Oocyte-two electrode patch clamp recordings Functional expression of $\alpha_1$G-INS-1 in Xenopus oocytes.

Oocytes from Xenopus laevis will be used for functionally expressing T-type $Ca^{2+}$ channel $\alpha$1G-INS-1 subunit and for drug screening. Oocytes, at maturation stage V, will be obtained by surgery from anesthetized Xenopus frogs. Once removed, the oocytes will be stored in the sterile Barth medium supplemented with penicillin and streptomycin at 19–20° C. The outer vitelline (follicular) layer will be removed either mechanically after osmotic shrinkage in K-aspartate solution or chemically with collagenase/trypsin treatment. Defolliculated oocytes will be again incubated in the Barth medium until injection. Injection will be performed with a pneumatic injector. After microinjection of cRNA, the oocytes will be incubated for three to five days in the antibiotic-supplemented sterile Barth medium at 19–20° C.

Voltage clamp recording and solutions.

$Ca^{2+}$ currents will be recorded using the conventional two-microelectrode voltage-clamp technique. Voltage recording electrodes will be filled with 3 M KCl and current injecting electrodes with the solution containing (in mM): CsCl 500, EGTA 10, HEPES 10, pH 7.4 (adjusted with CsOH). For the isolation of $Ca^{2+}$ channel current and suppression of the oocyte intrinsic calcium activated $Cl^-$ conductance, $Cl^-$-free methanesulphonate-substituted extracellular solution containing $Ba^{2+}$ as charge carrier will be used (in mM): $Ba(OH)_2$ 40, NaOH 50, KOH 2, HEPES 10, pH 7.4 (adjusted with methanesulphonic acid). To also eliminate $Na^+$ conductance and maximally suppress $K^+$, in some cases tetraethylammonium hydroxide will be substituted for NaOH in this solution.

The inhibitory effect of compounds on the T-type $Ca^{2+}$ current will be examined with variable doses. Drugs will be perfused into a chamber where a cell is voltage clamped successfully, T-type $Ca^{2+}$ current will be recorded at 0 mV when held at −90 mV. The designed concentrations will be $10^{-7}, 10^{-6}, 10^{-5}$ and $10^{-4}$ for each compound. The normalized effect of compounds on current amplitude will be averaged from four or more experiments.

To determine the effect of the compounds on the voltage-dependent properties of the T-type $Ca^{2+}$ channel, the voltage-dependent activation and steady-state inactivation of the T-type $Ca^{2+}$ current expressed in Xenopus oocytes will be characterized. For the voltage dependent activation, the T-type $Ca^{2+}$ current will be recorded at test potentials between −60 mV to +30 mV with increments of 10 mV. For the inactivation, a two second pre-pulse will be applied before a test pulse of 0 mV for 200 mV. Holding potential will be kept at −80 mV for both activation and inactivation characterizations. Normalized conductance-voltage relationship curves were fitted with the Boltzmann equation, $1/\{1+\exp[(V-V_{1/2})/k]\}$, where $V_{1/2}$ is the voltage of half activation and k is a slope factor.

Part II (Alternative). Effect of compounds on the $Ca^{2+}$ currents in HEK-293 cells that expressing $\alpha_1$G-INS-1 subunit of T-type $Ca^{2+}$ channel.

Permanent expression of $\alpha_1$G-INS-1 subunit of T-type $Ca^{2+}$ channel in mammalian cells.

Islet isoform of $\alpha_1$G-INS-1 subunit of T-type $Ca^{2+}$ channel cDNA will be supplied in the pMT2 vertebrate expression vector (Genetics Institute, Cambridge, Mass.). Green Fluorescent Protein (GFP) cDNA will be excised from Bluescript vector. The GFP fragment will be ligated into pMT2. HEK-293 cells will be transfected by electroporation. 15 µg of pMT2-α1(T) and 1 µg of GFP constructs will be used for transfection. Successfully transfected cells will be identified for electrophysiological recording by expression of GFP.

The whole-cell patch clamp recordings.

The whole-cell recordings will be carried out by the standard "giga-seal" patch clamp technique. The whole-cell recording pipettes will be made of hemocapillaries (Warner Instrument Corp., Hamden, Conn.), pulled by a two-stage puller (PC-10, Narishige International, New York, N.Y.), and heat polished with a microforge (MF-200, World Precision Instruments, Sarasota, Fla.) before use. The pipette resistance will be in the range of 2–5 MΩ with our internal solution. The recordings will be performed at room temperature (22° C.). Currents were recorded using an EPC-9 patch-clamp amplifier (HEKA, Lambrecht/Pfalz, Germany) and filtered at 2.9 kHz. Data will be acquired with Pulse/PulseFit software (HEKA). Voltage-dependent currents will be corrected for linear leak and residual capacitance by using an on-line P/n subtraction paradigm. Normalized conductance-voltage relationship curves will be fitted with the Boltzmann equation, $1/\{1+\exp[(V-V_{1/2})/k]\}$, where $V_{1/2}$ is the voltage of half activation and k is a slope factor.

Solutions:

$Ca^{2+}$ current recording solution will contain (in mmol/l): 10 $CaCl_2$, 110 tetraethylammonium-Cl (TEA-Cl), 10 CsCl, 10 N -2-hydroxyethylpiperazine-N'-2-ethanesulfonic acid (HEPES), 40 sucrose, 0.5 3,4-diaminopyridine, pH 7.3. The pipette solution will contain (in mmol/l): 130 N-methyl-D-glucamine, 20 EGTA (free acid), 5 bis (2-aminophenoxy) ethane-N, N, N', N'-tetraacetate (BAPTA), 10 HEPES, 6 $MgCl_2$, 4 $Ca(OH)_2$, pH was adjusted to 7.4 with methanesulfonate. 2 mmol/l Mg-ATP was included in the pipette solution to minimize run-down of L-type $Ca^{2+}$ currents.

The inhibitory effect of compounds on the T-type $Ca^{2+}$ current will be examined with variable doses. Drugs will be perfused into a chamber where a cell is voltage clamped successfully, T-type $Ca^{2+}$ current will be recorded at 0 mV when held at −90 mV. The designed concentrations will be $10^{-7}$, $10^{-6}$, $10^{-5}$ and $10^{-4}$ M for each compound. The normalized effect of compounds on current amplitude will be averaged from four or more experiments.

To determine the effect of the compounds on the voltage-dependent properties of the T-type $Ca^{2+}$ channel, we will characterized the voltage-dependent activation and steady-state inactivation of the T-type $Ca^{2+}$ current expressed in HEK cells. For the voltage dependent activation, the T-type $Ca^{2+}$ current will be recorded at test potentials between −60 mV to +30 mV with increments of 10 mV. For the inactivation, a two second pre-pulse will be applied before a test pulse of 0 mV for 200 mV. Holding potential will be kept at −80 mV for both activation and inactivation characterizations. Normalized conductance-voltage relationship curves were fitted with the Boltzmann equation, $1/\{1+\exp[(V-V_{1/2})/k]\}$, where $V_{1/2}$ is the voltage of half activation and k is a slope factor.

2) Effect of compounds on the high voltage activated (e.g. L-type) $Ca^{2+}$ currents in insulin secreting cells.

High voltage activated $Ca^{2+}$ currents will be recorded in INS-1 cells or HIT cells with perforated patch clamp configuration (to prevent L-type $Ca^{2+}$ current "run-up"). In order to eliminate the contamination of T-type $Ca^{2+}$ currents, cell membrane potential will be held at −40 mV and recorded at +20 mV. The time-dependent effect of the compounds on high voltage activated $Ca^{2+}$ current will be examined by sampling the current amplitude every 30 second for 30 minutes after perfusing $10^{-6}$ M of each compound. If no time-dependent effect is detected, in the next step we will establish the dose-dependent effect of each compound on the high voltage activated $Ca^{2+}$ currents. The designed concentrations will be $10^{-6}$, $10^{-5}$, $10^{-4}$ and $10^{-3}$ M for each compound. The normalized current amplitude will be averaged from at least four experiments.

The effect of T-type $Ca^{2+}$ modulators can be determined by the measurements of changes in intracellular $Ca^{2+}$ (using microfluorometry and $Ca^{2+}$ sensitive probes such as fluo-3 or fura-2) following a an increase in extracellular $K^+$ in the presence of the test compound(s). The cells are kept in an extracellular medium with a slightly reduced $K^+$ level in order to hyperpolarize the cells and thereby obtain a resting membrane potential which is optimal for the activation of the T-type channel. The stimulatory level of $K^+$ should be carefully chosen to obtain a depolarization of the cell to a membrane potential where influx through T-type is maximal and at the same time minimizimg influx through other $Ca^{2+}$ channel types. If the cells used contain KATP channels, diazoxide (50–100 microM) may be included in the extracellular media to improve the control of the membrane potential. Suitable cell lines are INS or RINm5F which both contain T-type $Ca^{2+}$ channels. 5 µM ω-conotoxin and 10 µM nifedipine can be added to the incubation medium to block the influx of calcium through the N-type and L-type calcium channels. Cells, which have been transfected with the T-type $Ca^{2+}$ channel, can also be used.

The testing is conducted using the following procedure:

Buffer: Modified KRW (in mM): NaCl 140, KCl 0.5, $NaH_2PO_4$ 0.5, $MgSO_4$ 0.5, $NaHCO_3$ 2, $CaCl_2$ 1.5, HEPES 10, Probenecid 2, pH 7.4.

Protocol: INS-1 cells or BetaTC3 cells were cultured in black-walled 96-well plates (Packard View-Plate) under normal conditions. They were washed and loaded in modified KRW, 1 mM D-glucose to repolarise the cells, with the fluorescent calcium indicator Fluo-4/AM (1 µM) in the presence of 2 mM Probenecid for 30 min. After washing in the same modified KRW and addition of modified KRW, supplemented or not with 10 µM Nifedipine and/or 50 µM BPDZ 73, the cell plate was placed in the FLIPR. Automated addition of a KCl gradient was done in separate experiments after which 10 and 30 mM KCl, giving about 50 and 100% response, were chosen as fixed concentrations for successive studies of the test compounds. The compounds were tested as 10 point 1:3 dilution series, with 50 μM as the highest concentration. The changes in Fluo-4 fluorescence were followed every two or six seconds for 3–10 min during compound addition and the addition of KCl (two different protocols, thereby the variance in timing). A Katp channel opener, BPDZ 73, at 10 μM was added to ensure full repolarisation the cells, dependent on $K_{ATP}$ channels.

PHARMACEUTICAL COMPOSITIONS

The formulation of pharmaceutical compositions and their subsequent administration is believed to be within the skill in the art. In general, for therapeutics, a patient suspected of needing such therapy is given a composition in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions, which may also contain buffers, diluents and other suitable additives.

In addition to such pharmaceutical carriers, cationic lipids may be included in the formulation to facilitate uptake. One such composition shown to facilitate uptake is LI-POFECTIN (BRL, Bethesda, Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compositions, and can generally be calculated based on $IC_{50}$'s or $EC_{50}$'s in vitro and in vivo animal studies. For example, given the molecular weight of compound (derived from chemical structure) and an effective dose such as an $IC_{50}$, for example (derived experimentally), a dose in mg/kg is routinely calculated.

The compounds of the invention may be administered to a mammal, especially a human, in need of treatment prevention, elimination alleviation or amelioration of the diseases as mentioned above. Such mammals include also animals, both domestic animals and non-domestic animals.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

EXAMPLES

The process of preparing the compounds of formula (I) is further illustrated in the following examples which, however, are not to be construed as limiting.

EXAMPLE 1

(1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclopropanecarboxylate dihydrochloride 2-(2-{[3-(1-Benzoimidezol-2-yl)-propyl]-methyl-amino}-ethyl)-6-fluoro-1-isopropyl-1,2,3,4-tetrahydro-2-naphthalinol Methoxyacetic acid 2(S)-[2-[N-[3-(2-benzimidazolyl)propyl]-N-methylamino]ethyl]-6-fluoro-1(S)-isopropyl-1,2,3,4-tetrahydro-2-naphthyl ester dihydrochloride (Mibefradil, 0.570 g) in ethanol (96%, 5 ml) and aqueous sodiumhydroxide (1 N, 5 ml) was refluxed for 2 h. The cold reaction mixture was concentrated. The residue was partitioned between water and dichloromethane. The aquoeus layer was extracted with dichloromethane (2X). The combined organic layers were dried (sodium sulfate) and concentrated to give the title compound as a clear sirup 0.43 g (100%).

1H-NMR (CDCl$_3$): δ7.57 (broad, 2H); 7.23 (m, 2H); 6.97 (m, 1H); 6.58 (m, 2H); 3.07–2.83 (m, 3H); 2.75 (m, 1H); 2.6 (m, 4H); 2.5–2.2 (s+m, 3H+3H); 2.06 (p, 2H); 1.81 (broad dd, 1H); 1.50 (m, 2H); 1.20 (d, 3H); 0.53 ppm (d, 3H).

(1S, 2S)-2-(2-{N-[(3-benzoimidazol-2-yl)propyl]-N-methylamino}ethyl)-6-fluoro-1,2,3,4-tetrahydro-1-isopropyl-2-naphtyl cyclopropanecarboxylate dihydrochloride 2-(2-{[3-(1-Benzoimidazol-2-yl)-propyl]-methyl-amino}-ethyl)-6-fluoro-1-isopropyl-1,2,3,4-tetrahydro-2-naphthalinol (0.110 g) was dissolved in dichloromethane (1 ml). Diisopropylethylamine (0.045 mi) and cyclopropanecarbonyl chloride (0.071 ml) was added. After stirring for 19 h the reaction mixture was poured out in aqueous saturated sodium. After dilution with water and dichloromethane, the organic layer was washed with water, dried (sodium sulfate) and concentrated. The residue was purified by flash chromatography using dichloromethane/methanol 6:1 as eluent to give the free base as a sirup (0.12 g, 82%). This product was dissolved in ethanol and aqueous hydrochloride (1 N, 0.55 ml) was added. After stirring for 1 h the mixture was concentrated. The residue was crystallized from ethyl acetate to give the title compound (50 mg, 54%). A less pure crop of crystals could be isolated from the mother liquor (57 mg, 39%).

Mp 134–141° C.; El SP/MS: 491 (M+)

1H-NMR (DMSO): δ7.77 (m, 2H); 7.52 (m, 2H); 7.07 (m, 1H); 6.96 (broad d, 2H); 3.3 (m, 2H); 3.2 (m, 4H); 3.0 (m, 2H); 2.9 (m, 1H); 2.67 (s, 3H); 2.45 (m, 1H); 2.38 (m, 2H); 2.15–1.80 (m, 4H);1.57 (m, 1H); 1.04 (d, 3H); 0.90 (m, 4H); 0.38 ppm (d, 3H).

What is claimed is:

1. A compound of formula (I):

(I)

wherein R$^1$ is H, C$_{1-6}$-alkyl or phenyl which is optionally substituted with halogen, methoxy or C$_{1-6}$-alkyl; and R$^2$—C—R$^3$ together forms a C$_{3-6}$-cycloalkyl group; or a pharmaceutically acceptable salt thereof.

2. A compound of formula (I):

(I)

wherein R$^1$ is H or C$_{1-6}$-alkyl and R$^2$—C—R$^3$ together forms a C$_{3-6}$-cycloalkyl group, or a pharmaceutically acceptable salt thereof.

3. The compound of claim 1, wherein R$^1$ is H.

4. The compound of claim 1, wherein R$^1$ methyl.

5. The compound of claim 1, wherein R$^2$—C—R$^3$ together forms a cyclopropyl group.

6. The compound of claim 1, wherein R$^2$—C—R$^3$ together forms a cyclobutyl group.

7. The compound of claim 1, selected from one of:
- (1S ,2S)-2-(2-{N-[(3-benzoimidazol-2-yl),propyl]-N-methylamino}ethyl)-6-fluoro-1,2,3,4-tetrahydro-1-isopropyl-2-naphtyl cyclopropanecarboxylate; or
- a pharmaceutically acceptable salt thereof.

8. The compound of claim 1, selected from the group consisting of:
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclobutanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclopentanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl cyclohexanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclopropanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl ethylcyclopropanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclobutanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl ethylcyclobutanecarboxylate;
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclopentanecarboxylate; and
- (1S,2S)-2-(2-{N-[(3-benzoimidazol-2-yl)propyl]-N-methylamino}ethyl)-6-fluoro-1,2,3,4-tetrahydro-1-isopropyl-2-naphtyl methylcyclohexanecarboxylate; or a pharmaceutically acceptable salt thereof.

9. The pharmaceutical composition comprising the compound of claim 1, or a pharmaceutical acceptable salt thereof, together with one or more pharmaceutically acceptable carriers or diluents.

10. A method of inhibiting a rise in intracellular calcium mediated by an influx through T-type calcium channels in a subject in need thereof, comprising administering an effective amount of the compound of claim 1 to said subject.

11. A method of treating type 2 diabetes in a subject in need thereof comprising administering an effective amount of the compound of claim 1 to said subject.

12. A method of treating type 1 diabetes in a subject in need thereof comprising administering an effective amount of the compound of claim 1 to said subject.

13. A method of treating diabetic cardiovascular disorders in a subject in need thereof comprising administering an effective amount of the compound of claim 1 to said subject.

14. A method of treating microvascular or macrovascular diseases in a subject in need thereof comprising administering an effective amount of the compound of claim 1 to said subject.

15. A method of treating retinopathy in a subject in need thereof comprising administering an effective amount of the compound of claim 1 to said subject.

16. A method of treating nephropathy in a subject in need thereof comprising administering an effective amount of the compound of claim 1 to said subject.

17. A method of treating neuropathy a subject in need thereof comprising administering an effective amount of the compound of claim 1 to said subject.

18. A method of treating macrovascular disease in a subject in need thereof comprising administering an effective amount of the compound of claim 1 to said subject.

* * * * *